Figure 1:
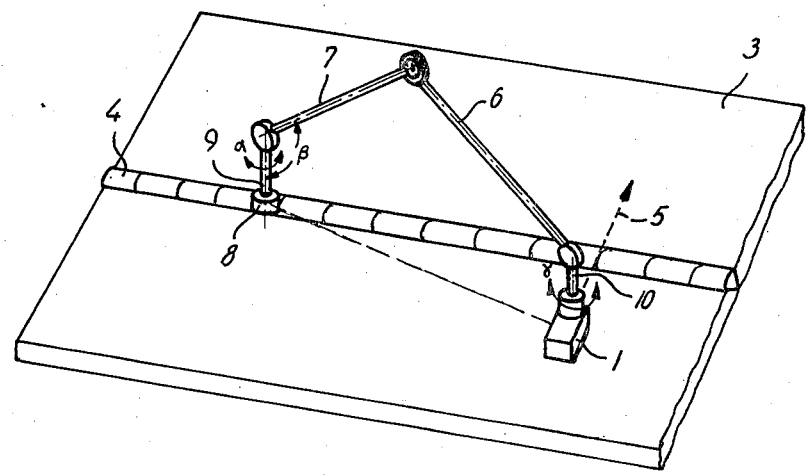

United States Patent [19]

Lund et al.

[11] 4,226,122

[45] Oct. 7, 1980

[54] APPARATUS FOR RECORDING ECHO PULSES

[75] Inventors: Svend A. Lund, Birkerød; Sven E. Iversen, Charlottenlund; Carl E. T. Petersen, Skovlunde; Erik T. Bøgen, Dåstrup, Viby SJ.; Jørgen Dam, Herlev, all of Denmark

[73] Assignee: Akademiet for de Tekniske Videnskaber, Svejsecentralen, Glostrup, Denmark

[21] Appl. No.: 919,602

[22] Filed: Jun. 27, 1978

[30] Foreign Application Priority Data

Jul. 1, 1977 [DK] Denmark .............................. 2961/77

[51] Int. Cl.[3] ............................................. G01N 29/04
[52] U.S. Cl. ...................................... 73/609; 73/614; 73/620
[58] Field of Search ................ 73/609, 610, 614, 620, 73/582

[56] References Cited

U.S. PATENT DOCUMENTS

| | | | |
|---|---|---|---|
| 3,482,434 | 12/1969 | Cowan et al. | 73/609 |
| 3,872,715 | 3/1975 | Pittaro | 73/609 |
| 3,939,697 | 2/1976 | Lund et al. | 73/614 |
| 3,962,909 | 6/1976 | Lund | 73/609 |
| 4,030,344 | 6/1977 | Northeved et al. | 73/620 |
| 4,058,001 | 11/1977 | Waxman | 73/620 |

FOREIGN PATENT DOCUMENTS

| | | | |
|---|---|---|---|
| 2636401 | 2/1978 | Fed. Rep. of Germany | 73/609 |
| 1216753 | 12/1970 | United Kingdom. | |
| 1376117 | 12/1974 | United Kingdom. | |
| 1495539 | 12/1974 | United Kingdom. | |
| 1460624 | 1/1977 | United Kingdom. | |

*Primary Examiner*—Anthony V. Ciarlante
*Attorney, Agent, or Firm*—Schuyler, Birch, McKie & Beckett

[57] ABSTRACT

A three-dimensional ultrasonic scanning apparatus produces projection pictures on the surface of an object under inspection or examination and on planes perpendicular thereto. The amplitudes of the echo pulses produced by the ultrasonic scanning appartus, which uses an angle probe, are stored in a memory having at least one storage position relating to each projection of a reflecting point within the examined area. Only the highest echo amplitude originating from all the reflecting points lying on a projection line at right angles to the projection plane in question is recorded—not the highest amplitude from each reflecting point on the projection line. Thus, only those echo pulse amplitudes necessary to produce a projection picture of the object are stored in the memory thereby substantially reducing the required memory capacity.

9 Claims, 7 Drawing Figures

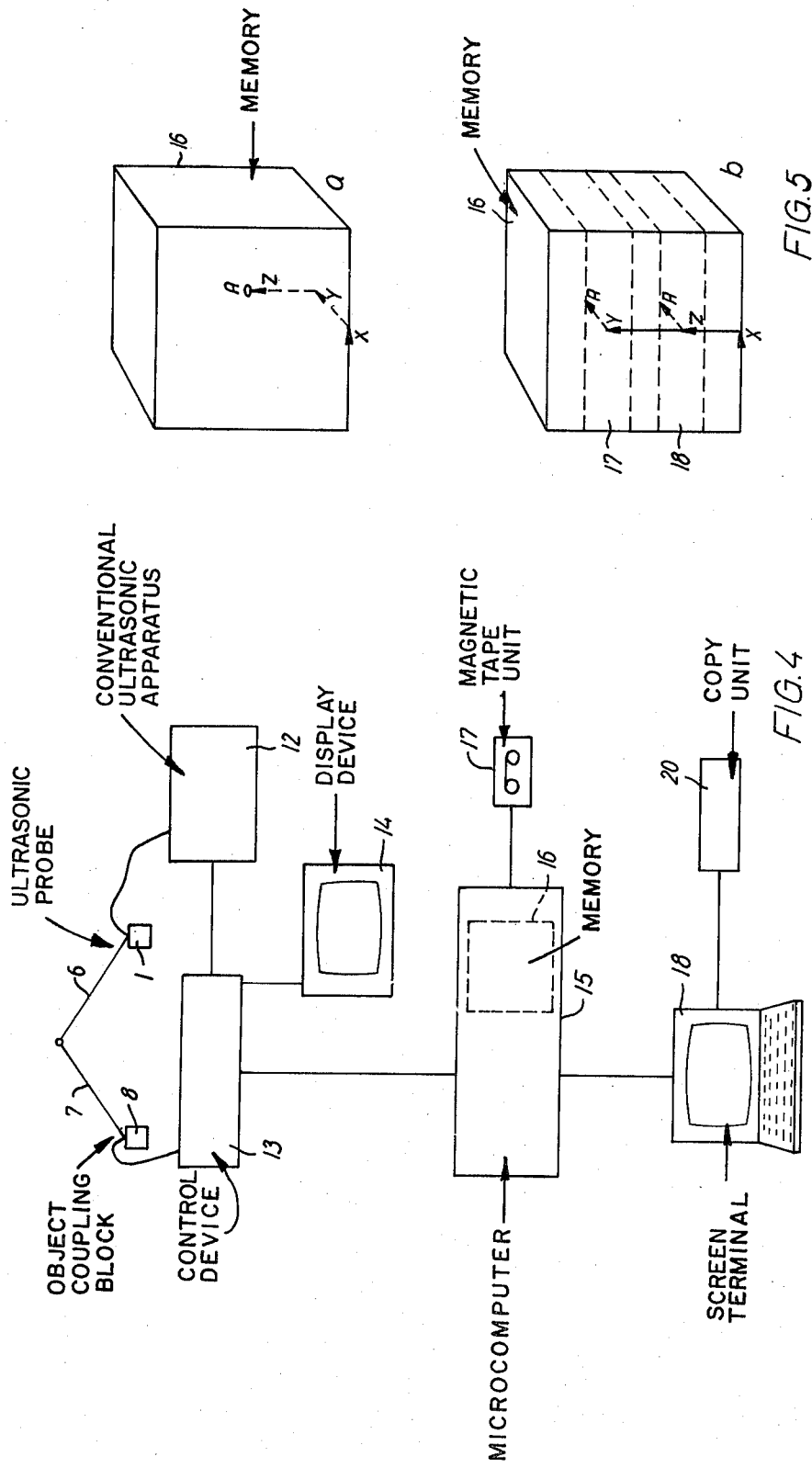

APPARATUS FOR RECORDING ECHO PULSES

The present invention relates to an apparatus for recording echo pulses from inhomogeneities in otherwise homogeneous objects having a plane or slightly curved surface, by ultrasonic inspection according to the pulse echo method using a least one angle probe which can be moved freely in a two-dimensional scanning movement over the surface of the object, comprising position signal producing means for producing signals containing information on the position of the sound emission point of the probe and the direction of the projection of the sound beam on the surface of the object, co-ordinate signal producing means for producing, on receipt of echo pulses, on the basis of the position signals and the transit time of the ultrasonic pulses, signals containing information on the spatial co-ordinates of the reflecting points of the object causing the echo pulses, and a memory for storing or recording the data produced by the inspection.

In ultrasonic inspections of the type in question, it is known to record all the data immediately produced by the inspection. The data serves as a permanent documentation of the effected inspection, and by reproducing the data the whole inspection procedure can be repeated. The amount of data which recorded is extremely large, due to the fact that a time-based recording is concerned, where the entire amount of data produced during the inspection is recorded.

The present invention has for its object to provide a simplification of the equipment used, and a reduction of the time necessary for the reproduction of data, through a reduction of the amount of data stored.

This is achieved according to the invention by having the memory provided with at least one storage position for the amplitude of the echo signal from each reflecting point within the inspected area of the object, and by having the apparatus arranged to bring about, on receipt of each echo pulse, the recording of its amplitude in at least one storage position determined by the appurtenant co-ordinate signals, but only if an echo amplitude higher than the last incoming amplitude has not already been recorded in the storage position in question. In this case the recording is position-based which implies in itself a substantial simplification, because in the known time-based recording, a recording of all echoes from each individual reflecting point takes place. The fact that only the highest echo signal from each reflecting point is recorded represents a substantial further simplification.

According to the invention the memory can have a storage position for each possible reflecting point within the inspected area of the object, and at each storage position means can be provided for recording the echo amplitude. In this case the memory contains all the data necessary for reproducing the data produced by the ultrasonic inspection.

For utilizing the data recorded or stored in the memory the apparatus according to the invention may contain display means for producing, from the recorded amplitude data and the appurtenant storage positions, pictures of the reflecting points corresponding to projection pictures on the surface of the object and on planes perpendicular thereto.

If the recorded data is only used to display the projection pictures and the appurtenant amplitudes, the memory may have, according to the invention, for each desired projection picture, a number of storage positions corresponding to the projections of the possible reflecting points on the appurtenant projection plane, means being provided at each storage position for recording the highest occurring echo amplitude. In this case a further substantial reduction of the recorded data amount is obtained. This is due to the fact that only the largest of the echo signals originating from a reflecting point lying on a line perpendicular to the projection plane in question is recorded.

The apparatus according to the invention can be arranged for displaying echo signals of an amplitude lying above a given level with a first display characteristic and echo signals of an amplitude lying below said level with another display characteristic; the latter characteristic including the possibility of no display. This makes the interpretation of the displayed pictures much simpler. If desired, the apparatus according to the invention can be arranged for displaying the echo signals with more than two different display characteristics, by classifying the echo signals according to several levels. According to the invention the levels can be adjustable. For instance, the different display characteristics can consist of different shades of gray.

Figure 7:
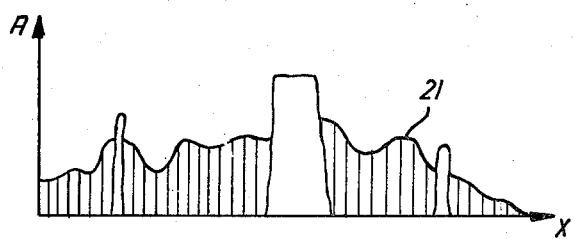
Figure 2:
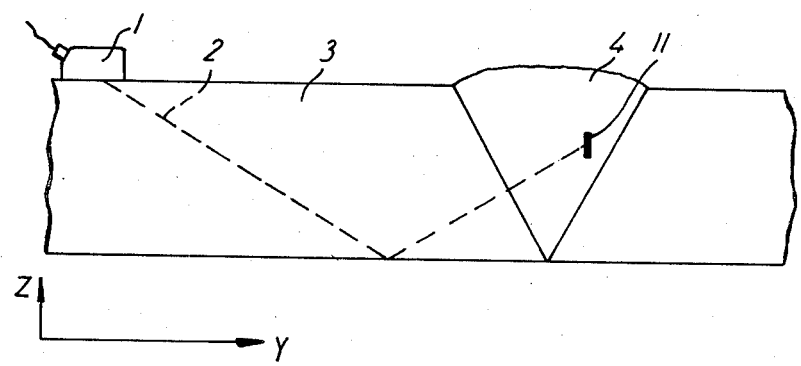
Figure 3:
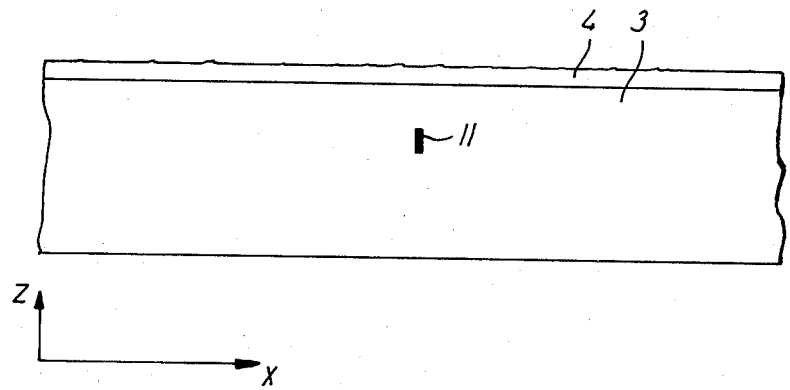
Figure 6:
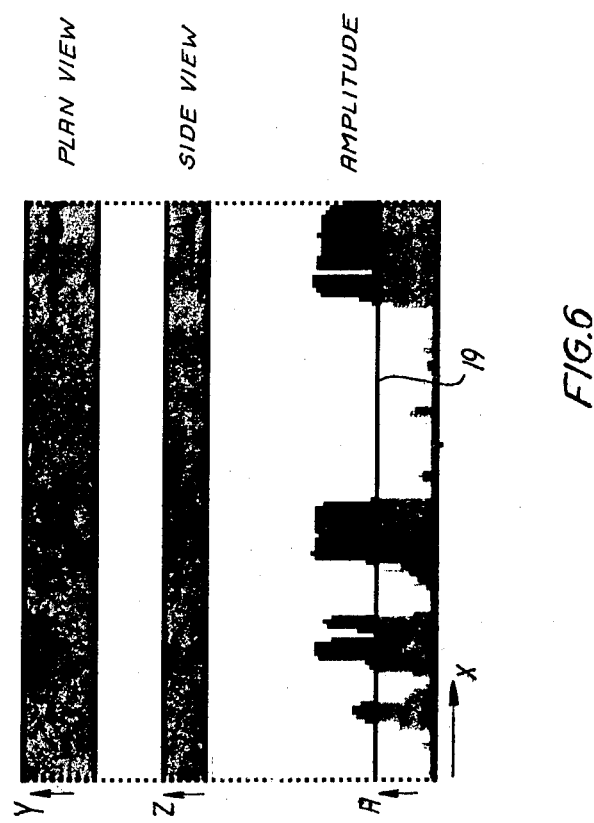

The invention will be explained in more detail with reference to the schematic drawing in which FIG. 1 shows an ultrasonic probe with appurtenant position signal producing means disposed on an object to be inspected, FIGS. 2 and 3 are sections through the object in two directions perpendicular to one another, FIG. 4 is a block diagram of an embodiment of the apparatus according to the invention, FIG. 5a and 5b show schematically a memory, FIG. 6 is an example of a screen picture produced with an apparatus according to the invention, and FIG. 7 is an example of the insertion of a reference curve in a part of a screen picture as shown in FIG. 6.

FIG. 1 shows an ultrasonic probe 1 as shown in FIG. 2 emits an ultrasonic beam 2, into an object 3 containing a weld 4 to be inspected. The beam 2 forms a constant angle with the surface of the object. The arrow 5 in FIG. 1 indicates the projection of the ultrasonic beam on the surface of the object. The ultrasonic probe 1 is, through a lever device provided with two arms 6 and 7 which are pivotally connected with each other, coupled to a block 8 which during the test is secured to the object, e.g. by gravitation or by means of a magnet, and thus constitutes a fixed point. The arm 7 is pivotally connected with a vertical arm 9 which is rotatable in the block 8. Correspondingly, the arm 6 is pivotally connected with a vertical arm 10 about which the ultrasonic probe 1 can rotate.

As a result of the said lever device having the indicated possibilities of movement, the ultrasonic probe 1 can be moved freely in a two-dimensional movement over the surface of the object, while being continually coupled to the stationary block 8 via the lever device. The position of the ultrasonic probe 1 and thereby the sound emitting point, which preferably lies directly under the arm 10, is determined by two angles, viz. the angle position $\alpha$ of the arm 9 in relation to the block 8, which determines the direction to the ultrasonic probe, and the angle $\beta$ between the arms 7 and 9, which determines the distance to the ultrasonic probe. The direction of the projection 5 of the ultrasonic beam is determined by the angle $\gamma$ in connection with the angle position $\alpha$ of the ultrasonic probe in relation to the arm 10.

The ultrasonic beam 2 from the probe 1 is reflected up and down between the bottom and the top of the object, and as it will appear from FIG. 2, it is the part of the beam reflected once from the bottom which is used for testing the weld 4. It is, however, also possible to utilize other parts of the beam path for the test.

In FIGS. 2 and 3 an inhomogeneity 11 is indicated in the form of a weld flaw which will send a strong ultrasonic echo back to the ultrasonic probe 1.

Knowing the sound velocity in the object 3 and the angle at which the beam 2 is sent into the object, it is possible, on the basis of the transit time of the ultrasonic pulse and the three angles $\alpha$, $\beta$ and $\gamma$ which are measured by means of angle transducers incorporated in the pivot joints concerned, to determine the exact position of the flaw 11, e.g. in a rectangular co-ordinate system X, Y, Z, as indicated n FIGS. 2 and 3, showing a section at right angles to the weld through the flaw 11, and a section along the weld also through the flaw, respectively.

FIG. 4 shows the ultrasonic probe 1 electrically connected to a conventional ultrasonic apparatus 12 adapted to produce electric pulses for actuating the ultrasonic probe 1, so that it emits ultrasonic pulses into the object, and for treating the electric pulses produced when the reflected ultrasonic energy reaching the ultrasonic probe 1 causes the production of electrical pulses in said probe. From the ultrasonic apparatus 12, data on the transit time of the ultrasonic pulses and the echo amplitudes are transmitted to a control device 13. Information on the angles $\alpha$, $\beta$ and $\gamma$ is furthermore transmitted to the control device 13 from the angle transducers incorporated in the lever system. On the basis of the data received, the control device 13 is in a position to determine the co-ordinates of the reflecting points. The result of the manual or automatic scanning of the weld by means of the ultrasonic probe 1 can be displayed on a storage screen in the display device 14. The data produced by the control device 13 is further transmitted to a microcomputer 15 containing a memory 16 and connected to a magnetic tape unit 17 and a screen terminal 18.

By use of the computer 15, related values of the echo amplitude and the co-ordinates of the reflecting point in question are determined, and these values are recorded in the memory 16. Said memory can, for instance, be arranged as schematically indicated in FIG. 5a and 5b. In FIG. 5a the co-ordinates X, Y, Z of a reflecting point are drawn along three directions perpendicular to one another within the cube, and in the storage position thus arrived at, the echo amplitude A is recorded. This requires the provision at each storage position of a storage element which is able to record as many different amplitude values as it is desired to display. Although the computer 15 is arranged so that, for each individual storage position, only the largest of the amplitudes produced during the inspection from the corresponding reflecting point is recorded, the arrangement of the memory in question is nevertheless comparatively complicated. Since what is desired to be displayed by means of the recorded data will normally be projection pictures on projection surfaces which are perpendiculer to one another, the simpler construction of the memory indicated in FIG. 5b can be used. This construction uses two separate areas 17 and 18 of the memory for recording the data necessary to the production of projection pictures on a plane parallel to the surface of the object and a plane perpendicular thereto, which is parallel to the weld, respectively. The faces of the two areas 17 and 18 appearing foremost in the drawing correspond geometrically to the two projection planes and, at any point of these faces, the value of the greatest echo received from all the reflecting points situated on a line perpendicular to the projection plane in the corresponding point is recorded at right angles to the face.

The contents of the memory 16 can be transferred to a magnetic tape in the magnetic tape unit 17 and can again be returned from the magnetic tape to the memory 16. Instead of a magnetic tape, another recording medium can be used. By means of the data contained in the memory 16, it is now possible to produce on the screen of the screen terminal 18 pictures of the results of the test, e.g. as shown in FIG. 6. The upper band marked "plan view" shows a projection picture of inhomogeneities on a plane parallel to the surface of the object. Correspondingly, the next band marked "side view" shows a projection picture of inhomogeneities on a projection plane perpendicular to the surface of the object and parallel to the weld. By comparison of echo signal indications positioned vertically above each other, the position of the reflecting point is exactly determined. The lower band marked "amplitude" indicates the largest amplitude from the reflecting point whose echo pulse is indicated in the two above-situated bands vertically above the amplitude indication in question.

By means of the key-board and the screen terminal 18 it is possible to communicate with the computer 15. In this way the data necessary to the calculation of the co-ordinates of the reflecting points can be introduced by means of the key-board. It may, for instance, be the thickness of the object, the angle of the ultrasonic beam with the surface of the object or the velocity of sound in the material constituting the object.

By means of the key-board it is furthermore possible to insert a reference level 19 in the display, cf. FIG. 6. In the embodiment shown, the insertion of the reference level results in the part of the amplitude of the echo pulses which is greater than the reference level being shown with another display characteristic—here a darker gray shade—than the part of the echo amplitude lying below the reference level. In the two projection pictures the insertion of the reference line results in only the echoes whose amplitude is higher than the reference level being displayed. It is possible to arrange the display so that the echo amplitudes below the reference level are not shown at all. Correspondingly, it will be possible to display all the echoes in the projection pictures but with different gray shades depending on whether the amplitudes exceed the reference level or not. It is also possible to insert a plurality of levels and use a suitable number of different display characteristics.

If it is specified for the objects inspected that flaws whose echo amplitudes do not exceed a given value are tolerable, the reference level 19 can suitably be placed at that value, and the two upper bands will therefore only show the echoes originating from flaws which are not tolerable.

If the reference level is moved as low as possible, all echo amplitudes will be reproduced, as well as the amplitudes corresponding to the background echo signals originating from crystal boundaries. If echo signals are entirely missing in a section along the X axis, this is an indication that the inspection has not been complete.

In FIG. 4 the screen terminal 18 is shown connected to a copy unit 20 whereby hard copies of the screen picture can be produced.

During the inspection of certain materials, e.g. stainless steel, it appears that the amplitudes of the background echoes vary widely depending on the path of travel of the beam in the object. This is mainly due to stronger echoes from the crystal boundaries. In that case the apparatus can be arranged so that in the visualization of the echo amplitudes, instead of a reference level, as shown in FIG. 6, a reference curve 21, as shown in FIG. 7, is inserted, which in all essentials corresponds to the envelope of the background echoes. This makes it substantially easier to distinguish the flaw echoes from the background echoes, than if use was made of a fixed level lying above the amplitudes of the background echoes.

The invention is not limited to the embodiments shown in the drawings and described hereinbefore, but it can be modified in many ways which are apparent to an expert in this field.

What we claim is:

1. An apparatus for recording projection pictures of internal inhomogeneities in otherwise homogenous objects having a substantially plane or slightly curved surface on projection planes perpendicular to each other, the apparatus recording projection pictures by ultrasonic inspection according to the pulse-echo method, said apparatus comprising:

ultrasonic inspection means having at least one ultrasonic angle probe for emitting and receiving ultrasonic sound pulses, said ultrasonic angle probe being freely movable in a two dimensional scanning movement over the surface of the object;

position signal producing means for producing position signals containing information on the position of said ultrasonic angle probe and the direction of the projection of the ultrasonic sound pulses on the surface of the object;

coordinate signal producing means responsive to echo pulses received from reflecting points in the object for producing, on the basis of the position signals and the transit time of the ultrasonic sound pulses, coordinate signals containing information on the spatial coordinates of the reflecting points in the object causing the echo pulses;

memory means for storing echo pulse amplitudes, said memory means having a storage area for each of the perpendicular projection planes, said storage area having at least one storage position for each projection on the projection plane of reflecting points in the object; and recording means connected to said coordinate signal producing means for recording an echo pulse amplitude in each of said storage positions of said memory means, wherein said recording means records the echo pulse amplitude in at least one of said storage positions determined by the coordinate signals from said coordinate signal producing means if the echo pulse amplitude is higher than the last echo pulse amplitude recorded in said storage position.

2. The apparatus claimed in claim 1 further comprising means for transferring the information contained in said memory means to a recording medium, e.g., a magnetic tape or disk, and for retransferring the information to the said memory means.

3. The apparatus claimed in claim 1 wherein said memory means has one storage position for each projection of reflecting points on one of said projection planes, said recording means recording an echo pulse amplitude at each of said storage positions.

4. The apparatus claimed in claim 1 further comprising display means responsive to the data stored in said memory means for displaying pictures of the reflecting points corresponding to projection pictures on the surface of the object and on projection planes perpendicular thereto.

5. The apparatus claimed in claim 4 wherein said display means is arranged for displaying the echo pulse amplitude.

6. The apparatus claimed in claim 4 wherein said display means displays echo signals of an amplitude lying above a given level with a first display characteristic, and echo signals of an amplitude lying below said level with another display characteristic.

7. The apparatus claimed in claim 6 wherein said display means displays the echo signals with more than two different display characteristics by classifying the echo signals according to several levels.

8. Tha apparatus claimed in claim 7 wherein the levels are adjustable.

9. The apparatus claimed in claim 4 further comprising means for inserting in the display of the echo amplitude a reference curve, substantially corresponding to the envelope of the background signals, viz. the signals not corresponding to the inhomogeneities the echo signals of which are to be displayed.

* * * * *